(12) United States Patent
Fajnsztajn (10) Patent No.: US 6,837,868 B1
(45) Date of Patent: Jan. 4, 2005

(54) INDWELLING URINARY CATHETER WITH BASE DRAINAGE PORT

(76) Inventor: Aleksander Fajnsztajn, P.O. Box 6684, San Fafael, CA (US) 94903

( * ) Notice: Subject to any disclaimer, the term of this patent is extended or adjusted under 35 U.S.C. 154(b) by 0 days.

(21) Appl. No.: 09/205,835

(22) Filed: Dec. 3, 1998

(51) Int. Cl.$^7$ .............................................. A61M 29/00

(52) U.S. Cl. .............................. 604/96.01; 604/101.03; 604/328

(58) Field of Search ................................ 606/191–194; 604/96.01, 101.01, 101.02, 101.03, 101.05, 101.06, 328, 913, 916, 917, 918

(56) References Cited

U.S. PATENT DOCUMENTS

| | | | | |
|---|---|---|---|---|
| 4,351,342 A | * | 9/1982 | Wiita et al. .................. | 128/349 |
| 4,813,935 A | * | 3/1989 | Haber et al. ................... | 604/99 |

* cited by examiner

Primary Examiner—Manuel Mendez (57) ABSTRACT

An indwelling urinary catheter comprises a two-ply (or equivalent) air-inflatable anchoring balloon means in which an outer ply or skin thickness thereof, is not bonded to the inner ply over one or more small areal segments each measured at the intersection of the two plys radially located from the axis of symmetry of a central catheter body. Instead, when inflated, each areal segment expands mostly in a sidewise looking direction over a minimum radial arc relative to a central catheter body, to form one or more elongated lobes that are larger than and hence stabilize the catheter body relative to the entry port of the user's bladder but leaving rigid collar regions located between adjacent segments so as to not interfere with the formation of large drainage ports therethrough. After deployment and inflation, these one or more segments are seen to provide corresponding one or more corresponding inflated lobes those size is much greater than that of the entry port of the user's bladder to prevent the stabilize of the catheter therefrom during use. Meanwhile, since each of the rigid collar regions is of greater wall thickness than that provided the outer ply of the segments, the location of the drainage ports provided therein, relative to the entry port of the user's bladder, can be dramatically changed, viz., the latter can also be downwardly re-located to be more closely adjacent to the entry port of the user's bladder, than heretofore. Result: greater drainage efficiency wherein little or no residue urine stowage, occurs in the user's bladder.

16 Claims, 7 Drawing Sheets

INDWELLING URINARY CATHETER WITH BASE DRAINAGE PORT

This invention relates to an indwelling urinary catheter comprising a two-ply (or equivalent) air-inflatable anchoring balloon means in which an outer ply thereof, is not bonded to the inner ply over one or more small areal wall segments each measured at the intersection of the two plys radially located from the axis of symmetry of a central catheter body. When inflated, each areal wall segment (the ratio of longitudinal height H versus arcuate width W being at least 3:1 with a range of 5:1 to 10:1 being preferred) expands mostly in a sidewise looking direction over a minimum radial arc relative to a central catheter body, to form one or more elongated lobes those maximum size is larger than that of the entry port of the user's bladder and hence stabilize the catheter body relative to the latter. But the origin of the lobes is small enough relative to the full circumference of the catheter body that space remains to permit the formation of one or more rigid collar regions therebetween. Result: formation of large drainage ports is easily permitted between the outer surface of the catheter body connecting the same to its interior cavity, in a region closely adjacent to and slightly above the entry port of the user's bladder (normalized to gravity). That is to say, after deployment and inflation, the outer ply of the one or more areal wall segments is engineered so that the size of the one or more corresponding inflated lobes is much greater than that of the entry port of the bladder to prevent catheter dislodgement during use. Since each of the rigid collar regions is of greater wall thickness than that provided for the limited areal segments, the drainage ports provided therein, can also be downwardly relocated more closely adjacent to the entry port of the user's bladder, than heretofore possible. Result: greater drainage efficiency wherein little or no residue urine stowage, occurs in the user's bladder during catheterization even though such bladder may sag or tilt toward the entry port, due to fatigue, aging or the like.

In another aspect of the invention, the number of small areal wall segments is one wherein one sidewise lobe is thereafter provided. In yet another aspect the number of small areal segments is two wherein two symmetrical sidewise projecting lobes are provided along with two sets of vertically extending collar regions and two sets of entry port(s). In still another aspect the number of small areal wall segments three wherein three symmetrical sidewise projecting lobes are provided along with three sets of vertically extending collar regions and associated entry ports. In yet still another aspect the number of small areal wall segments is four wherein four symmetrical sidewise projecting lobes are provided along with four sets of vertically directed collar regions and associated aligned entry ports. In yet still another aspect the number of small areal segments is five wherein five symmetrical sidewise projecting lobes are provided along with five sets of vertically directed collar regions and associated vertically aligned entry ports. In yet still another aspect the number of small areal wall segments is six wherein six symmetrical sidewise projecting lobes are provided along with six sets of vertically directed collar regions and associated aligned entry ports.

In accordance with another aspect of the invention, the catheter body and balloon means are preferably integrally molded from silicone to produce the balloon shapes and entry port locations noted above wherein the balloon means is selectively provided by varying the thickness of the associated wall region of the catheter body in appropriate manner.

That is to say, each of the small areal wall segments that results in the lobes, noted above, has a central base region overspanning an air opening, also located within the wall of the catheter body, the base region itself being of reduced wall thickness in a sidewise direction over a limited arc region but Ha being of greater thickness in the remaining sidewise radial direction. The air opening of each base region (defining the aforementioned areal segment) is also selectively connectable to an exterior air pump via an air-conveying trough terminating at a valve within a pigtail tube integrally formed at the periphery of the central catheter body. The lateral and vertically extending, arcuate collar regions located adjacent to the base cavity of each balloon means, define a limited arc angle and hence comprise only a portion of the full wall of the catheter body. Terminating interior of the collar means is a large drainage cavity vertically extending throughout the catheter body to transport urine, such large drainage cavity being fluidly connectable to the aforementioned drainage (or entry} ports located adjacent to its terminal end (which in use, are positioned within the user's bladder above the entry port between first and second spaced apart projection planes defining the vertical (or axial) extent of the lobe(s) after deployment. Since each of the collar regions is of greater wall thickness than that provided for the limited areal segments of the balloon means, the drainage ports provided therein, can be re-located more closely adjacent to the entry port of the user's bladder, than heretofore. Result: greater drainage efficiency wherein little or no residue urine, occurs in the user's bladder during catheterization.

BACKGROUND OF THE INVENTION

Catheters of the prior art included the use of symmetrically disposed balloons in which—after deployment and inflation—the drainage ports of each inflated catheter are always located well above the upper reach of the inflated balloon (normalized to gravity), viz., high in the user's bladder above the entry port of the latter. Result: large amounts of the user's urine remain in the bladder, especially if the bladder sags or tilts toward the entry port, due to fatigue, aging or the like (hereinafter called "residual urine stowage").

SUMMARY OF THE INVENTION

In accordance with the invention, an indwelling urinary catheter comprises a two-ply (or equivalent) air-inflatable anchoring balloon means in which an outer ply or equivalent skin thickness thereof, is not bonded to the inner ply or thickness over one or more small areal segments each measured at the intersection of the two plys radially located from the axis of symmetry of a central catheter body. Instead, when inflated, each areal segment expands mostly in a sidewise looking direction over a minimum radial arc relative to a central catheter body, to form one or more elongated lobes that are larger than and hence stabilize the catheter body relative to the entry port of the user's bladder but leaving rigid collar regions located between adjacent segments so as to not interfere with the formation of large drainage ports therethrough. After deployment and inflation, these one or more segments are seen to provide corresponding one or more corresponding inflated lobes those size is much greater than that of the entry port of the user's bladder to prevent the stabilize of the catheter therefrom during use. Meanwhile, since each of the rigid collar regions is of greater wall thickness than that provided the outer ply of the segments, the location of the drainage ports provided therein, relative to the entry port of the user's bladder, can be dramatically changed, viz., the latter can also be downwardly re-located to be more closely adjacent to the entry port of the user's bladder, than heretofore. Result: greater drainage efficiency wherein little or no residue urine stowage, occurs in the user's bladder.

DETAILED DESCRIPTION OF THE INVENTION

Figure 1:
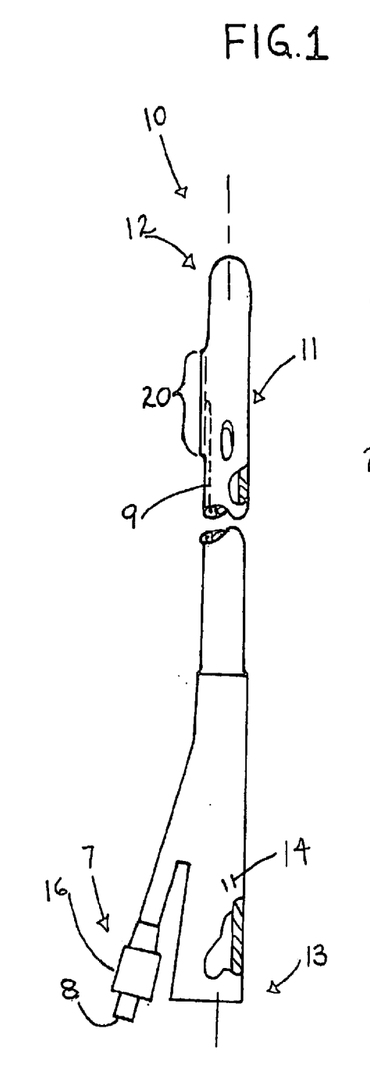
FIG. 1 is a plan view of a catheter incorporating the present invention showing a single elongated wall segment and a single collar region containing diametrically opposed drainage ports.

FIG. 1 shows an indwelling urinary catheter 10. As indicated the catheter 10 comprises a cylindrical discharge tube 11 having an inlet end 12 and Y-shaped discharge end 13. The Y-shaped discharge end 13 is of conventional design and includes a main enlarged cylindrical housing 14 connectable to a male connector (not shown) of urine collection system that includes a bag (also not shown) into which the urine can be temporarily stored. The Y-shaped discharge end 13 also includes air-pump housing having an inlet 8 of circular cross sect ion for engaging a conventional hand operated pump (not shown) for providing air pressure through a valve assembly 16 and thence to the inlet end 12 of the catheter 10 for inflation of balloon means 20 via an air-transference trough 9 shown in phantom line.

The shape of the balloon means 20 varies.

Figure 2:
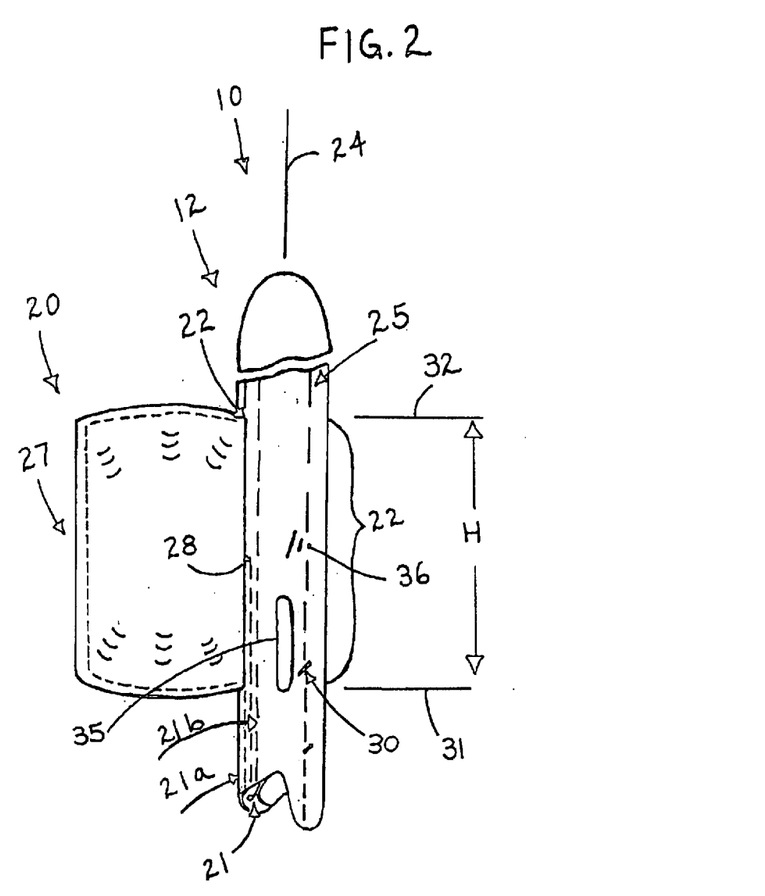
FIGS. 2 and 3 are fragmentary, enlarged views of the single wall segment and collar region of FIG. 1 after inflation, the former being a side view and the latter being a top view.
Figure 3:
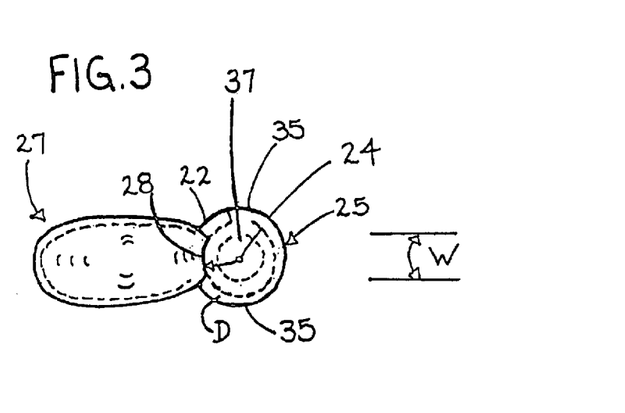

As shown in FIGS. 2 and 3, the balloon means 20 of catheter 10 comprises a side wall 21 of a two-ply (or equivalent) construction in which an outer ply 21a is not bonded to inner ply 21b over a small areal wall segment 22. The wall segment 22 is measured vertically and circumferentially at the intersection of the two plys 21a, 21b to define a longitudinal height H and an arcuate width W and is positioned at a radial distance D from axis of symmetry 24 of central catheter body 25. When inflated as shown in FIG. 3, the wall segment 22 (the ratio of longitudinal height H versus arcuate width W being at least 3:1 with a range of 5:1 to 10:1 being preferred) expands mostly in a sidewise looking direction over a minimum radial arc relative to the central catheter body 25, to form an elongated lobe 27 having an origin 28 at the wall segment 22. In use, the size of the lobe 27 is much larger than that of the entry port of the user's bladder (not shown) for stabilization purposes. But the size of the origin 28 of the lobe 27 is small enough relative to the full circumference of the side wall 21 of the catheter body 25 that sufficient space remains to permit the formation of a rigid collar region 30 measured between longitudinal first and second spaced apart projection planes 31, 32 defining the vertical (or axial) extent of the lobe 27 after deployment.

Result: formation of large drainage ports 35 is easily permitted through side wall 21 to fluidly connect outer surface 36 of the catheter body 25 to interior main cavity 37 at a level between longitudinal first and second spaced apart projection planes 31, 32 defining the vertical (or axial) extent of the lobe 27 after deployment. After insertion, such level is positioned closely adjacent to and slightly above the entry port of the user's bladder (normalized to gravity, not shown). Result: greater drainage efficiency wherein little or no residue urine stowage, occurs in the user's bladder during usage even though such bladder may sag or tilt toward the entry port, due to fatigue, aging, etc.

Figure 4:
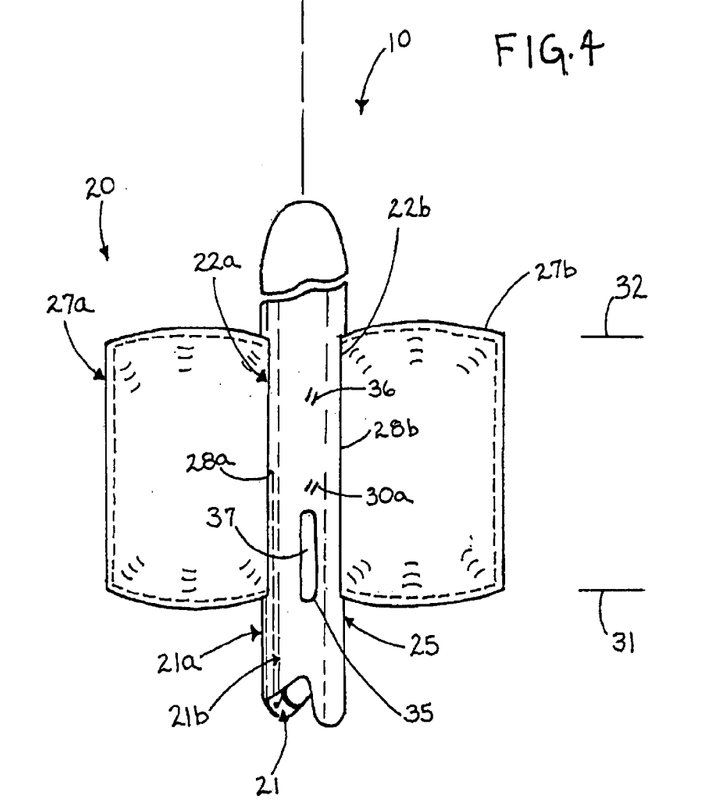
FIGS. 4 and 5 are fragmentary, enlarged views of an alternative to the catheter of FIG. 1 similar to FIGS. 2 and 3 showing two wall segments flanking two collar regions.
Figure 5:
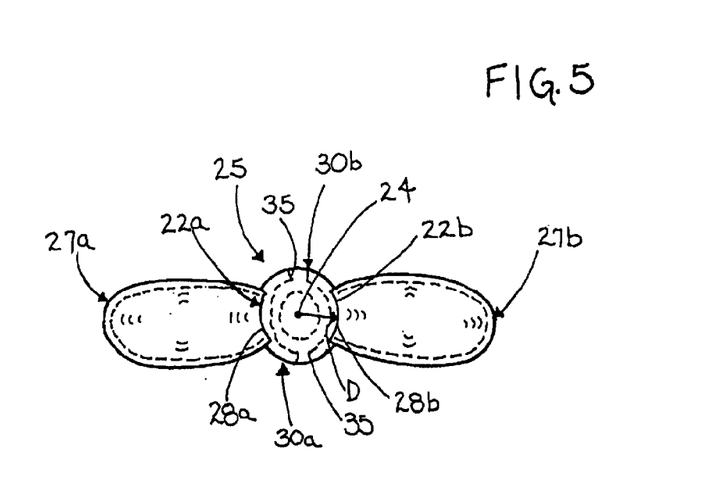

As shown in FIGS. 4 & 5, the balloon means 20' of catheter 10' comprises two diametrically opposed wall segments 22a' and 22b', each including two-ply (or equivalent) construction in which outer ply 21a' is not bonded to inner ply 21b' over the area comprising wall segments 22a' and 22b'. Each wall segment 22a' or 22b' is measured vertically and circumferentially at the intersection of the two plys 21a', 21b' and is positioned at a radial distance D1 from axis of symmetry 24' of central catheter body 25'. When inflated as shown in FIG. 5, each wall segment 22a' or 22b' expands mostly in an opposite sidewise looking direction opposite to that of the other segment, relative to the axis of symmetry 24' over a minimum radial arc relative to the central catheter body 25', to form an elongated lobe 27a' or 27b'. Origin 28a' or 28b' of each lobe 27a' or 27b corresponds to diametrically opposed wall segments 22a' or 22b', respectively. In use, the size of the lobes 27a' or 27b' is much larger than that of the entry port of the user's bladder (not shown) for stabilization purposes. But the size of the origin 28a' or 28b' of respectively lobes 27a' or 27b' is small enough relative to the full circumference of the side wall 21' of the catheter body 25' that sufficient space remains to permit the formation of rigid collar regions 30a', 30b' located between longitudinal first and second spaced apart projection planes 31', 32' defining the vertical (or axial) extent of the lobes 27a', 27b' after deployment. Result: formation of large drainage ports 35' is easily permitted through side wall 21' to fluidly connect outer surface 36' of the catheter body 25' and interior main cavity 37' closely adjacent to and slightly above the entry port of the user's bladder ,(normalized to gravity, not shown). Result: greater drainage efficiency wherein little or no residue urine, occurs in the user's bladder during even though such bladder may sag or tilt toward the entry port, due to fatigue, aging or the like.

Figure 6:
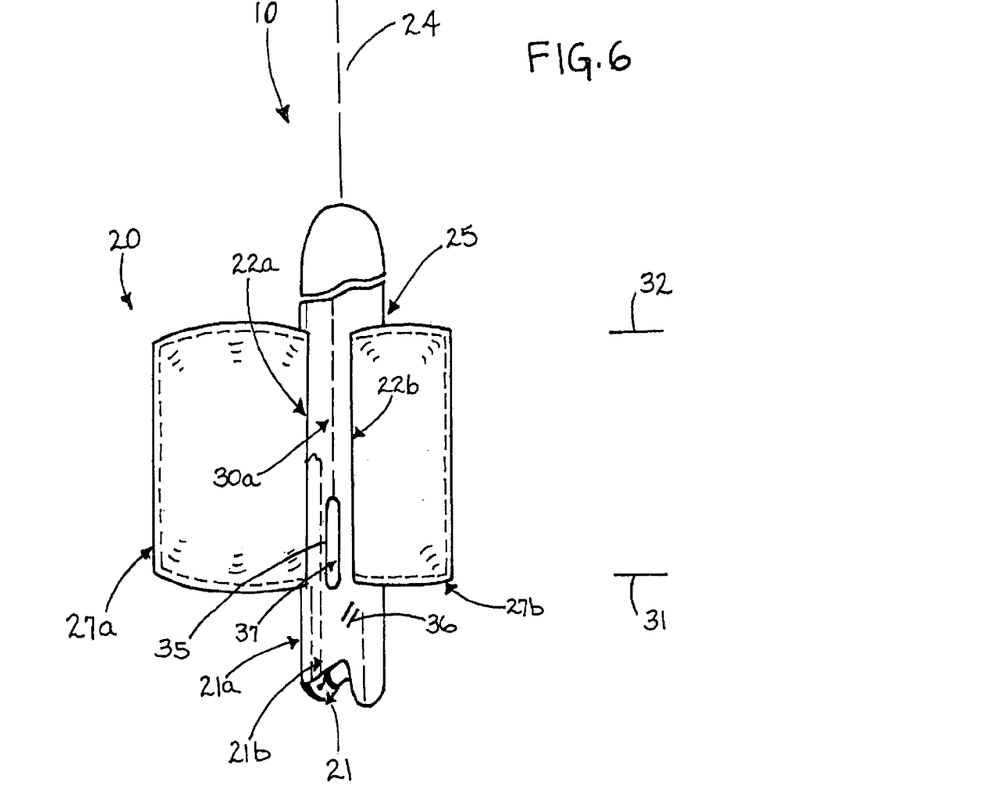
FIGS. 6 and 7 are fragmentary, enlarged views of an another alternative to the catheter of FIG. 1 similar to FIGS. 2–5 showing three wall segments flanking three collar regions.
Figure 7:
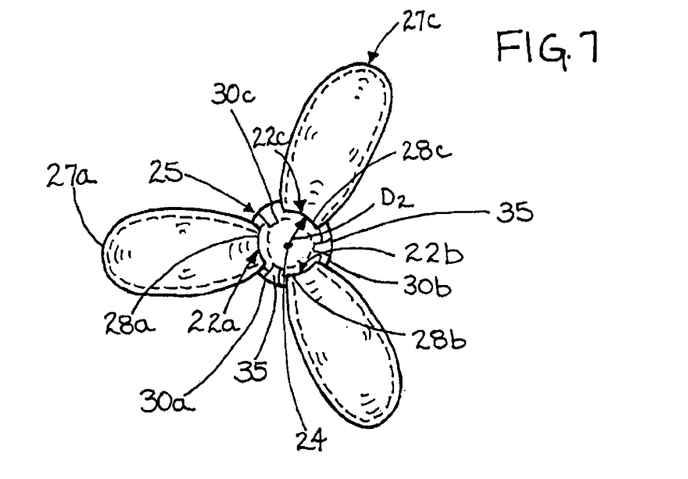

As shown in FIGS. 6 & 7, balloon means 20" of catheter 10" comprises three diametrically opposed wall segments 22a", 22b", 22c", each being arcuately spaced 120 degrees from neighboring segments and including two-ply (or equivalent) construction in which outer ply 21a" is not bonded to inner ply 21b" over the area comprising wall segments 22a", 22b" or 22c". Each wall segment 22a", 22b", 22c" is measured vertically and circumferentially at the intersection of the two plys 21a", 21b" and is positioned at a radial distance D2 from axis of symmetry 24" of central catheter body 25". When inflated as shown in FIG. 7, each wall segment 22a', 22b", 22c" expands mostly in a sidewise looking direction that is 120 degrees from those of neighboring segments, having a common origin at the axis of symmetry 24" over a minimum radial arc relative to the central catheter body 25", to form an elongated lobe 27a", 27b" or 27c". Origin 28a", 28b" or 28c" of each lobe 27a", 27b" or 27c" corresponds to diametrically opposed wall segments 22a", 22b" or 22c", respectively. In use, the size of the lobes 27a", 27b" or 27c" is much larger than that of the entry port of the user's bladder (not shown) for stabilization purposes. But the size of the origin 28a", 28b" or 28c" of respectively lobes 27a", 27b" or 27c" is small enough relative to the full circumference of the side wall 21" of the catheter body 25" that sufficient space remains to permit the formation of rigid collar regions 30a", 30b", 30c" located between longitudinal first and second spaced apart projection planes 31", 32" defining the vertical (or axial) extent of the lobes 27a", 27b", 27c" after deployment. Result: formation of large drainage ports 35" is easily permitted through side wall 21" to fluidly connect outer surface 36" of the catheter body 25" and interior main cavity 37" closely adjacent to and slightly above the entry port of the user's bladder (normalized to gravity, not shown). Result: greater drainage efficiency wherein little or no residue urine, occurs in the user's bladder during even though such bladder may sag or tilt toward the entry port, due to fatigue, aging or the like.

Figure 8:
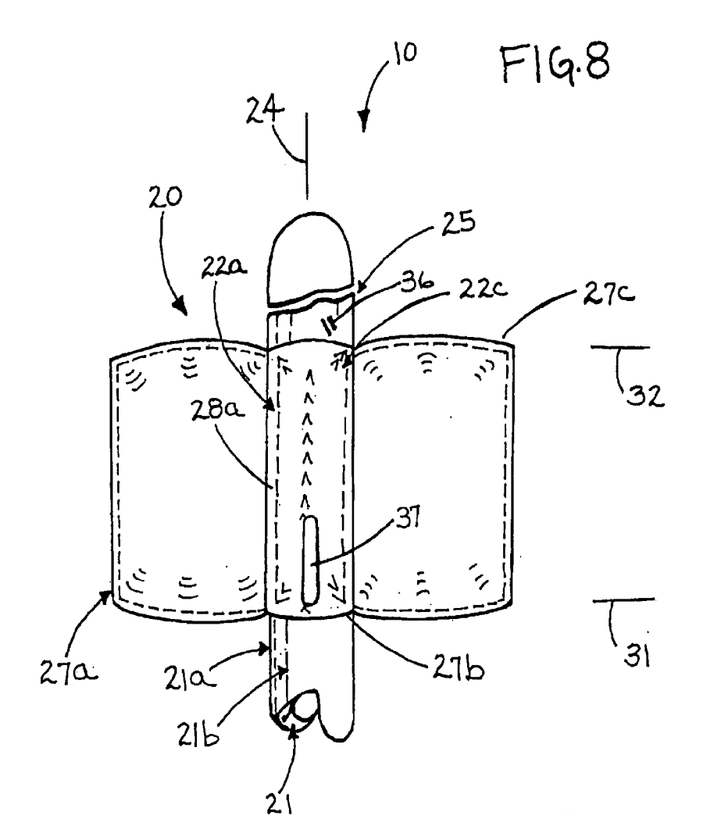
FIGS. 8 and 9 are fragmentary, enlarged views of still another alternative to the catheter of FIG. 1 similar to FIGS. 2–7 showing four wall segments flanking four collar regions.
Figure 9:
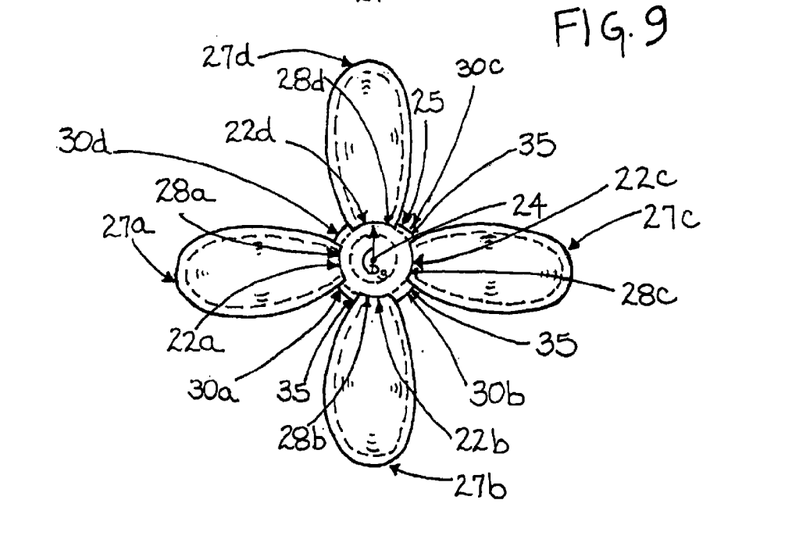

As shown in FIGS. 8 & 9, balloon means 20''' of catheter 10''' comprises four diametrically opposed wall segments 22a''', 22b''', 22c''', 22d''', each being arcuately spaced 90 degrees from neighboring segments and including two-ply (or equivalent) construction in which outer ply 21a''' is not bonded to inner ply 21b''' over the area comprising wall segments 22a''', 22b''', 22c''' or 22d'''. Each wall segment 22a''', 22b''', 22c''' or 22d''' , is measured vertically and circumferentially at the intersection of the two plys 21a''', 21b''' and is positioned at a radial distance D3 from axis of symmetry 24''' of central catheter body 25'''; When inflated as shown in FIG. 9, each wall segment 22a''', 22b''', 22c''' or 22d''' expands mostly in a sidewise looking direction that are spaced 90 degrees from those of neighboring segments, having a common origin at the axis of symmetry 24''' over a minimum radial arc relative to the central catheter body 25''', to form an elongated lobe 27a''' , 27b''', 27c''' or 27d'''. Origin 28a''', 28b''', 28c''', or 28d''' of each lobe 27a''', 27b' 27c' or 27d' " corresponds to diametrically opposed wall segments 22a''', 22b''', 22c''' or 22d''', respectively. In use, the size of the lobes 27a''' 27b''', 27c''' or 27d''' is much larger than that of the entry port of the user's bladder (not shown) for stabilization purposes. But the size of the origin 28a''', 28b''', 28c''' or 28d''' of respectively lobes 27a''', 27b''', 27c''' or 27d''' is small enough relative to the full circumference of the side wall 21''' of the catheter body 25''' that sufficient space remains to permit the formation of rigid collar regions 30a''', 30b''', 30c''', 30d''' located between longitudinal first and second spaced apart projection planes 31''', 32''' defining the vertical (or axial) extent of the lobes 27a''', 27b''', 27c''',27d''' after deployment. Result: formation of large drainage ports 35''' is easily permitted through side wall 21''' to fluidly connect outer surface 36''' of the catheter body 25''' and interior main cavity 37''' closely adjacent to and slightly above the entry port of the user's bladder (normalized to gravity, not shown). Result: greater drainage efficiency wherein little or no residue urine, occurs in the user's bladder during even though such bladder may sag or tilt toward the entry port, due to fatigue, aging or the like.

Figure 10:
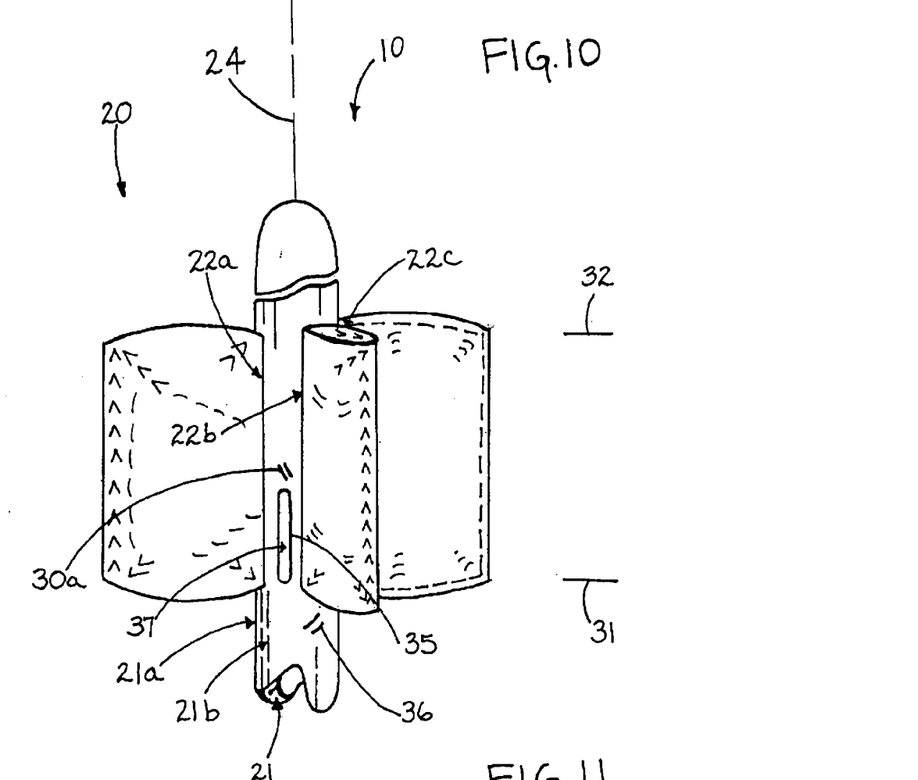
FIGS. 10 and 11 are fragmentary, enlarged views of yet another alternative to the catheter of FIG. 1 similar to FIGS. 2–9 showing five wall segments flanking five collar regions.
Figure 11:
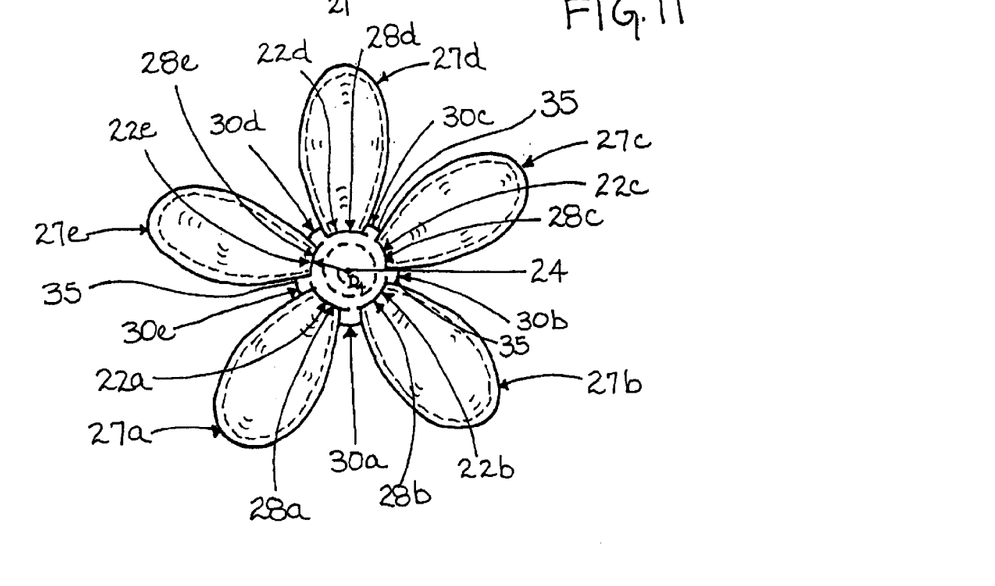

As shown in FIGS. 10 & 11, balloon means 20'''' of catheter 10'''' comprises five diametrically opposed wall segments 22a'''', 22b'''', 22c'''', 22d'''', 22e'''', each being arcuately spaced 72 degrees from neighboring segments and including two-ply (or equivalent) construction in which outer ply 21a'''' is not bonded to inner ply 21b'''' over the area comprising wall segments 22a'''', 22b'''', 22c'''', 22d'''' or 22e''''. Each wall segment 22a'''', 22b'''', 22c'''', 22d'''' or 22e'''', is measured vertically and circumferentially at the intersection of the two plys 21a'''', 21b'''' and is positioned at a radial distance D4 from axis of symmetry 24'''' of central catheter body 25''''. When inflated as shown in FIG. 11 each wall segment 22a'''', 22b'''', 22c'''', 22d'''' or 22e'''' expands mostly in a sidewise looking direction that are spaced 72 degrees from those of neighboring segments, having a common origin at the axis of symmetry 24'''' over a minimum radial arc relative to the central catheter body 25'''', to form an elongated lobe 27a'''', 27b'''', 27c'''', 27d'''' or 27e''''. Origin 28a'''', 28b'''', 28c'''', 28d'''' or 28e'''' of each lobe 27a'''', 27b'''', 27c'''', 27d'''' or 27e'''' corresponds to diametrically opposed wall segments 22a'''', 22b'''', 22c'''', 22d'''' or 22e'''', respectively. In use, the size of the lobes 27a'''', 27b'''', 27c'''', 27d'''' or 27e'''' is much larger than that of the entry port of the user's bladder (not shown) for stabilization purposes. But the size of the origin 28a'''', 28b'''', 28c'''', 28d'''' or 28e'''' of respectively lobes 27a'''', 27b'''', 27c'''', 27d'''' or 27e'''' is small enough relative to the full circumference of the side wall 21'''' of the catheter body 25'''' that sufficient space remains to permit the formation of rigid collar regions 30a'''', 30b'''', 30c'''', 30d'''', 30e'''' located between longitudinal first and second spaced apart projection planes 31'''', 32'''' defining the vertical (or axial) extent of the lobes 27a'''', 27b'''', 27c'''', 27d'''', 27e'''' after deployment. Result: formation of large drainage ports 35'''' is easily permitted through side wall 21'''' to fluidly connect outer surface 36'''' of the catheter body 25'''' and interior main cavity 37'''' closely adjacent to and slightly above the entry port of the user's bladder (normalized to gravity, not shown). Result: greater drainage efficiency wherein little or no residue urine, occurs in the user's bladder during even though such bladder may sag or tilt toward the entry port, due to fatigue, aging or the like.

Figure 12:
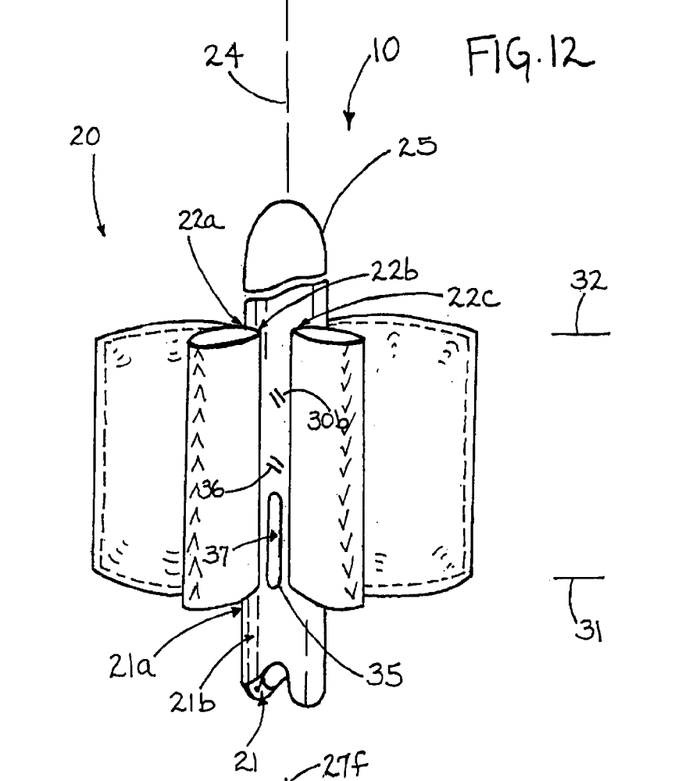
FIGS. 12 and 13 are fragmentary, enlarged views of still yet another alternative to the catheter of FIG. 1 similar to FIGS. 2–11 showing six wall segments flanking six collar regions.
Figure 13:
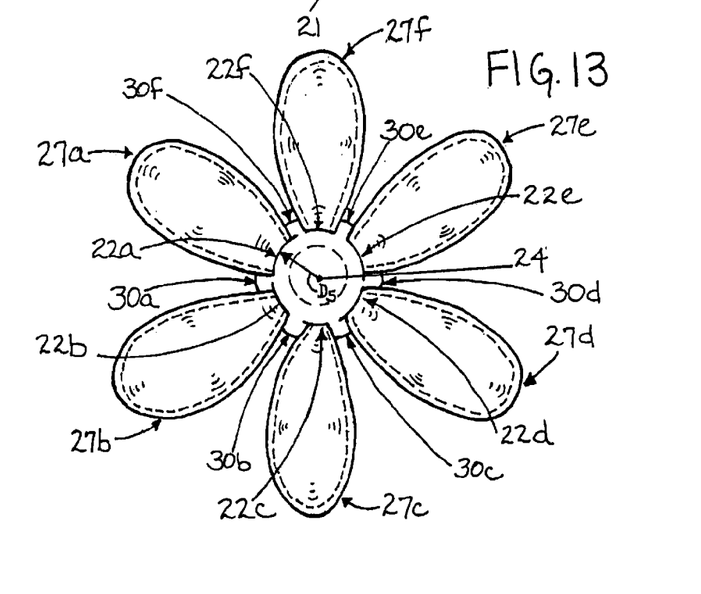

As shown in FIGS. 12 & 13, balloon means 20''''' of catheter 10''''' comprises six diametrically opposed wall segments 22a''''', arcuately spaced 60 degrees from neighboring segments and including two-ply (or equivalent) construction in which outer ply 21a''''' is not bonded to inner ply 21b''''' over the area comprising wall segments 22a''''', 22b''''', 22c''''', 22d''''', 22e''''' or 22f'''''. Each wall segment 22a''''', 22b''''', 22c''''', 22d''''', 22e''''' or 22f''''', is measured vertically and circumferentially at the intersection of the two plys 21a''''', 21b''''' and is positioned at a radial distance D5 from axis of symmetry 24''''' of central catheter body 25'''''. When inflated as shown in FIG. 13 each wall segment 22a''''', 22b''''', 22c''''', 22d''''', 22e''''', or 22f''''' expands mostly in a sidewise looking direction that are spaced 60 degrees from those of neighboring segments, having a common origin at the axis of symmetry 24''''' over a minimum radial arc relative to the central catheter body 25''''', to form an elongated lobe 27a''''', 27b''''', 27c''''', 27d''''', 27e''''' or 27f'''''. In use, the size of the lobes 27a''''', 27b''''', 27c''''', 27d'''', 27e'''' or 27f'''' is much larger than that of the entry port of the user's bladder (not shown) for stabilization purposes. But the size of each origin of the lobes 27a'''', 27b'''', 27c'''', 27d'''', 27e'''' or 27f'''' is small enough relative to the full circumference of the side wall 21'''' of the catheter body 25'''' that sufficient space remains to permit the formation of rigid collar regions 30a'''', 30b'''', 30c'''', 30d'''', 30e'''', 30f'''' located between longitudinal first and second spaced apart projection planes 31'''', 32'''' defining the vertical (or axial) extent of the lobes 27a'''', 27b'''', 27c'''', 27d'''', 27e'''', 27f'''' after deployment. Result: formation of large drainage ports 35'''' is easily permitted through side wall 21'''' to fluidly connect outer surface 36'''' of the catheter body 25'''' and interior main cavity 37'''' closely adjacent to and slightly above the entry port of the user's bladder (normalized to gravity, not shown). Result: greater drainage efficiency wherein little or no residue urine, occurs in the user's bladder during even though such bladder may sag or tilt toward the entry port, due to fatigue, aging or the like.

ALTERNATIVE

Figure 14:
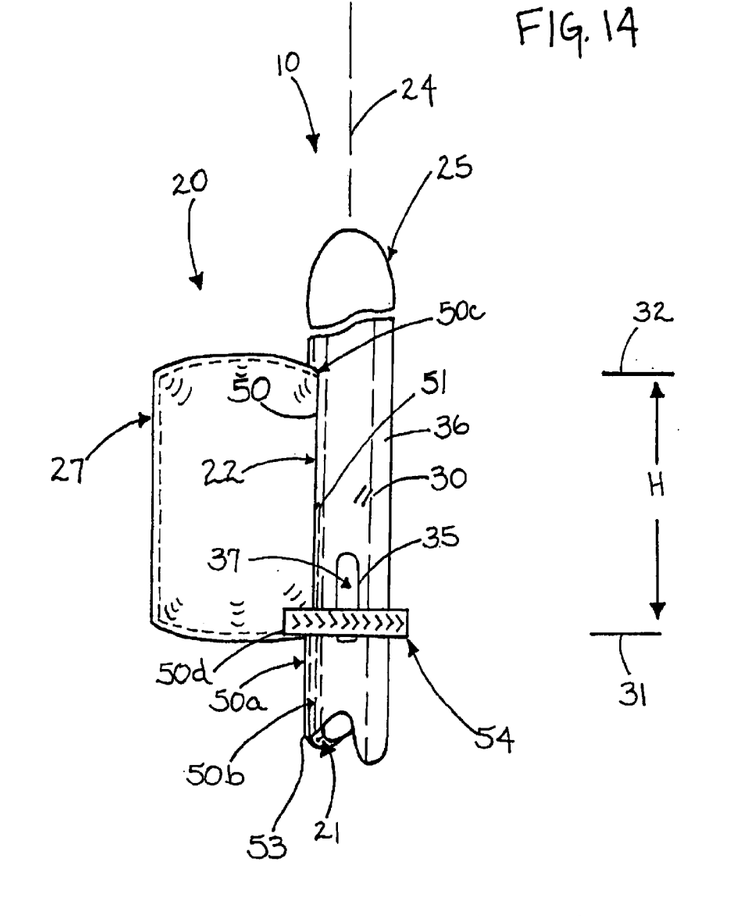
FIGS. 14 and 15 are fragmentary, enlarged views of still yet another alternative to the catheter of FIG. 1 similar to the view set forth in FIGS. 2–13 showing a single elongated wall segment of FIG. 1 connected to a full circumferentially extending ring segment at its lower end, with a collar region positioned above the ring segment, after inflation.
Figure 15:
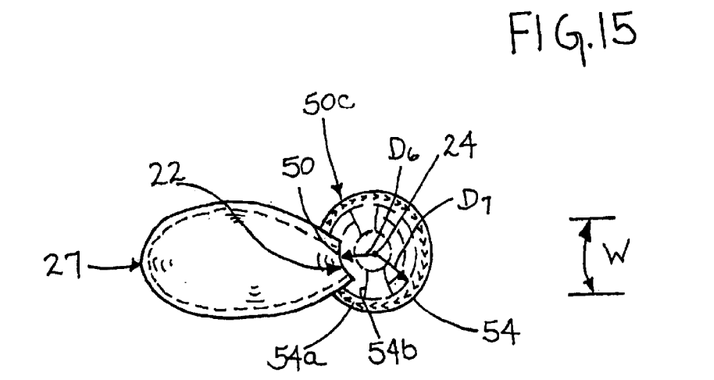

FIGS. 14 and 15 show an alternative catheter 10'''' in which catheter body 25'''' and balloon means 20'''' are integrally molded from silicone to produce the balloon shape and entry port locations noted in FIGS. 1–3 wherein the balloon means 20'''' is selectively provided by varying the thickness of the extending wall 21'''' of the catheter body 25'''' in appropriate manner.

That is to say, areal wall segment 22'''' that results in lobe 27'''', has a central base region 50 overspanning an air opening 51, also located within the side wall 21'''' of the catheter body 25''''. The wall segment 22'''' is measured vertically and circumferentially at the intersection of twin skin thicknesses (above and below same as discussed in detail below) and is defined by a longitudinal height H and an arcuate width W, and is positioned at a radial distance D6 from axis of symmetry 24'''' of central catheter body 25''''.

Base region 50 terminates in a radial direction (i) a thin over-skin portion 50a of reduced wall thickness positioned at a radial distance D7 from axis of symmetry 24'''' of central catheter body 25'''', where D7 is greater than D6, and (ii) an under-skin portion 50b of greater thickness located closer to the axis of symmetry 24'''' than the over-skin portion 50a. i.e., base region 50 is defined in the radial direction at the intersection of the over-skin portion 50a and under-skin portion 50b. However, termination in the longitudinal direction parallel to the axis of symmetry 24'''', occurs for the base region at end regions 50c, 50d bisected by the air opening 51, the latter being selectively connectable to an exterior air pump (not shown) via a single air-conveying trough 53 integrally formed at the periphery of the central catheter body 25''''. Also intersecting the lower end region 50d of the base region 50 is a circumferentially extending ring region 54. The ring region 54 terminates in (i) a thin over-skin portion 54a of reduced wall thickness and (ii) an under-skin portion 54b of greater thickness located closer to the axis of symmetry 24'''' than the over-skin portion 54a.

When inflated, the over-skin portions 50a, 54a of the base region 50 and ring region 54, expand. The over-skin portion 50a expands mostly in a sidewise looking direction over a minimum radial arc relative to the central catheter body 25'''', to form an elongated lobe 27'''' having an origin at the base region 50. Likewise, when inflated the over-skin portion 54a expands to form a truncated sphere 56 around the full circumference of the body 25'''' except for its intersection with region 50.

In use, the size of the lobe 27'''' is much larger than that of the entry port of the user's bladder (not shown) for stabilization purposes While the truncated sphere 56 is only sightly larger that entry port of the user's bladder for better sealing purposes. But the sizes of the origin of the lobe 27'''' and truncated sphere 56, are small enough relative to the full circumference of the side wall 21'''' of the catheter body 25'''' that sufficient space remains to permit the formation of a rigid collar region 30'''' measured between longitudinal first and second spaced apart projection planes 31'''', 32'''' defining the vertical (or axial) extent of the lobe 27'''' after deployment. Result: formation of large drainage ports 35'''' is easily permitted through side wall 21'''' to fluidly connect outer surface 36'''' of the catheter body 25'''' to interior cavity 37'''' at a level between longitudinal first and second spaced apart projection planes 31'''', 32'''' defining the vertical (or axial) extent of the lobe 27'''' after deployment. After insertion, such level is positioned closely adjacent to and slightly above the entry port of the user's bladder (normalized to gravity, not shown). Result: greater drainage efficiency wherein little or no residue urine, occurs in the user's bladder during usage even though such bladder may sag or tilt toward the entry port, due to fatigue, aging or the like.

It is obvious that alternate embodiments of the invention are suggestible to those skilled in the art from the discussion set forth above and such changes, modifications and alternatives are to be within the scope of the invention as claimed below.

What is claimed is:

1. In an indwelling urinary catheter comprising a cylindrical fluid discharge body having an axis of symmetry, a side wall, an outlet end region and an inlet end region defining urine inlet means, an air-transference system in selective parallel operation with said fluid discharge body and balloon means positioned adjacent to said inlet means of said fluid discharge tube operatively connected to said air-transference system, the improvement in said inlet means and said balloon means comprising one or more rigid collar means having one or more drainage ports therethrough and one or more areal segments longitudinally coextensively of said collar means, each of said one or more areal segments including a flexible over-skin region and a more rigid under-skin region at different radial distances from but at a common radial direction with respect to said axis of symmetry of said discharge body wherein said over-skin region of each areal segment is adapted to expand under air pressure to form a side lobe having a selected radial expansion direction with respect to said axis of symmetry and of a size collectively sufficient to prevent dislodgement of said catheter from an user's bladder during usage but wherein said one or more drainage ports of said one or more collar means is always longitudinally positioned in coextensive relationship with said side lobe and remains open to urine flow to thereby prevent the occurrence of residual urine stowage.

2. The improvement of claim 1 in which said side wall of said discharge body defines a circumference C in a horizontal plane normal to said axis of symmetry, in which each of said one or more areal segments intersects said horizontal plane, and in which one or more drainage ports of said one or more collar means each has an maximum opening W1 in said horizontal plane having an axis of symmetry coextensive of said horizontal plane and is adapted to remain open to fluid flow irrespective of the direction of deployment of said side lobe.

3. The improvement of claim 2 in which the number of areal segments is 1, the number of collar means is 1 and the number of drainage ports is at least 1.

4. The improvement of claim 2 in which the number of areal segments is 2, the number of collar means is 2 and the number of drainage ports associated with each collar means is at least 1 but wherein said axes of symmetry thereof are about 90 degrees to said expansion direct ions of neighboring side lobes associated with said areal segments.

5. The improvement of claim 2 in which the number of areal segments is 3, the number of collar means is 3 and the number of drainage ports associated with each collar means is at least 1 but wherein said axes of symmetry thereof are about 60 degrees to said expansion directions of neighboring side lobes associated with said areal segments.

6. The improvement of claim 2 in which the number of areal segments is 4, the number of collar means is 4 and the number of drainage ports associated with each collar means is at least 1 but wherein said axes of symmetry thereof are about 45 degrees to said expansion directions of neighboring side lobes associated with said areal segments.

7. The improvement of claim 2 in which the number of areal segments is 5, the number of collar means is 5 and the number of drainage ports associated with each collar means is at least 1 but wherein said axes of symmetry thereof are about 36 degrees to said expansion directions of neighboring side lobes associated with said areal segments.

8. The improvement of claim 2 in which the number of areal segments is 6, the number of collar means is 6 and the number of drainage ports associated with each collar means is at least 1 but wherein said axes of symmetry thereof are about 30 degrees to said expansion directions of neighboring side lobes associated with said areal segments.

9. In an indwelling urinary catheter comprising a cylindrical fluid discharge body having an axis of symmetry, a side wall, an outlet end region and an inlet end region defining urine inlet means, an air-transference system in selective parallel operation with said fluid discharge body and balloon means positioned adjacent to said inlet means of said fluid discharge tube operatively connected to said air-transference system, the improvement in said inlet means and said balloon means comprising one or more rigid collar means having one or more drainage ports therethrough and one or more areal segments longitudinally coextensively of said collar means, each of said one or more areal segments defining a skin portion formed of a material common to that of said side wall of said discharge body and adapted to expand under air pressure to form a side lobe having a selected radial expansion direction with respect to said axis of symmetry and of a size collectively sufficient to prevent dislodgement of said catheter from an user's bladder during usage but wherein said one or more drainage ports of said one or more collar means is always longitudinally positioned in coextensive relationship with said side lobe but always open to urine flow to thereby prevent the occurrence of residual urine stowage.

10. The improvement of claim 9 in which said side wall of said discharge body defines a circumference C in a horizontal plane normal to said axis of symmetry, in which each of said one or more areal segments intersects said horizontal plane, and in which one or more drainage ports of said one or more collar means each has an maximum opening W1 in said horizontal plane having an axis of symmetry coextensive of said horizontal plane and is adapted to remain open to fluid flow irrespective of the direction of deployment of said side lobe.

11. The improvement of claim 10 in which the number of areal segments is 1, the number of collar means is 1 and the number of drainage ports is at least 1.

12. The improvement of claim 10 in which the number of areal segments is 2, the number of collar means is 2 and the number of drainage ports associated with each collar means is at least 1 but wherein said axes of symmetry thereof are about 90 degrees to said expansion directions of neighboring side lobes associated with said areal segments.

13. The improvement of claim 10 in which the number of areal segments is 3, the number of collar means is 3 and the number of drainage ports associated with each collar means is at least 1 but wherein said axes of symmetry thereof are about 60 degrees to said expansion directions of neighboring side lobes associated with said areal segments.

14. The improvement of claim 10 in which the number of areal segments is 4, the number of collar means is 4 and the number of drainage ports associated with each collar means is at least 1 but wherein said axes of symmetry thereof are about 45 degrees to said expansion directions of neighboring side lobes associated with said areal segments.

15. The improvement of claim 10 in which the number of areal segments is 5, the number of collar means is 5 and the number of drainage ports associated with each collar means is at least 1 but wherein said axes of symmetry thereof are about 36 degrees to said expansion directions of neighboring side lobes associated with said areal segments.

16. The improvement of claim 10 in which the number of areal segments is 6, the number of collar means is 6 and the number of drainage ports associated with each collar means is at least 1 but wherein said axes of symmetry thereof are about 30 degrees to said expansion directions of neighboring side lobes associated with said areal segments.

* * * * *

UNITED STATES PATENT AND TRADEMARK OFFICE
CERTIFICATE OF CORRECTION

PATENT NO. : 6,837,868 B1
DATED : January 4, 2005
INVENTOR(S) : Fajnsztajn

It is certified that error appears in the above-identified patent and that said Letters Patent is hereby corrected as shown below:

Title page,
Item [76], Inventors, address should read -- P O Box 517, Corvallis, Oregon 97339 --

Column 4,
Lines 31 and 32, delete """.
Line 34, delete """ in both places.
Lines 35 and 38, delete """.
Lines 43 and 49, delete """ after "27a'" and "27b'".
Line 64, delete """ after "20".
Line 66, delete """ after "22a", "22b" and "22c"

Column 5,
Line 18, delete """ after "28a".
Line 51, delete """" after "27b".
Line 54, delete """"" after "22d".

Column 6,
Line 55, delete """"""' after "22c" "22e" and "22f".
Line 61, delete """"" after "22c" "22d" and "22e".

Signed and Sealed this

Twenty-sixth Day of July, 2005

JON W. DUDAS
*Director of the United States Patent and Trademark Office*